United States Patent [19]

Einhorn et al.

[11] Patent Number: 4,782,833

[45] Date of Patent: Nov. 8, 1988

[54] BONE BORING INSTRUMENT

[75] Inventors: Thomas A. Einhorn, 1155 Park Ave., New York, N.Y. 10128; Andrew Valenti, 277 Laclede Ave., Uniondale, N.Y. 11553; Matthew Alves, Kalamazoo, Mich.

[73] Assignees: Thomas A. Einhorn, New York; Andrew Valenti, Uniondale, both of N.Y.

[21] Appl. No.: 16,587

[22] Filed: Feb. 19, 1987

[51] Int. Cl.$^4$ ............................................. A61B 17/16
[52] U.S. Cl. .................................. 128/310; 128/305.1
[58] Field of Search .................... 128/305, 305.1, 310, 128/311, 312; 81/128, 59.1

[56] References Cited

U.S. PATENT DOCUMENTS

| | | | |
|---|---|---|---|
| 3,835,858 | 9/1974 | Hagen | 128/305.1 |
| 4,235,595 | 11/1980 | Arnegger | 128/305.1 |
| 4,314,577 | 3/1982 | Bofinger et al. | 128/305.1 |
| 4,600,006 | 7/1986 | Baker | 128/305.1 |

Primary Examiner—C. Fred Rosenbaum
Assistant Examiner—Mark F. Colosimo
Attorney, Agent, or Firm—Joseph W. Molasky & Assocs.

[57] ABSTRACT

An instrument for the boring of bones to remove a cylindrical section of bone for medical purposes has a one-way drive means which allows the surgeon to oscillate his hand motion while the instrument cuts bone in one direction only. The instrument has a trephine engaging mechanism which allows for the interchangeability of trephines so that a plurality of different types and sizes of trephines can be used to obtain bone cores from a range of bone types.

11 Claims, 3 Drawing Sheets

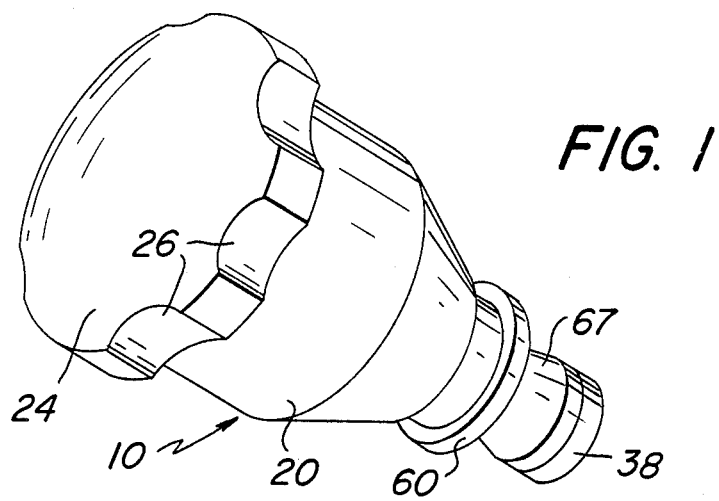
FIG. 1
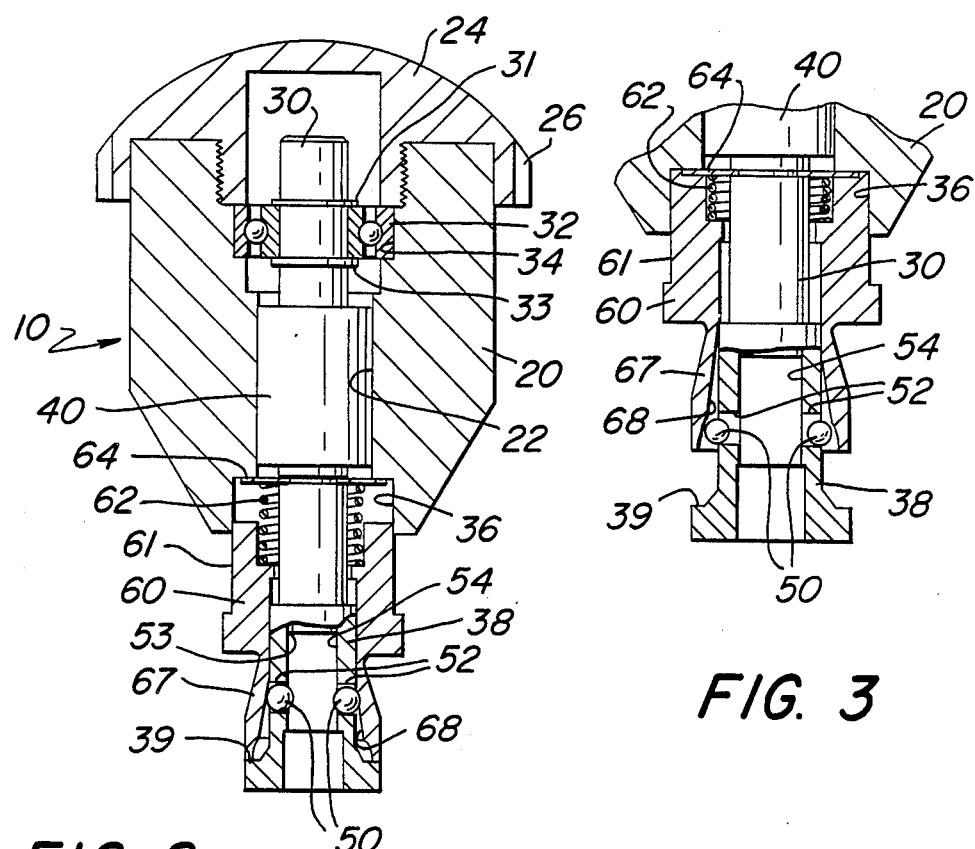
FIG. 2
FIG. 3

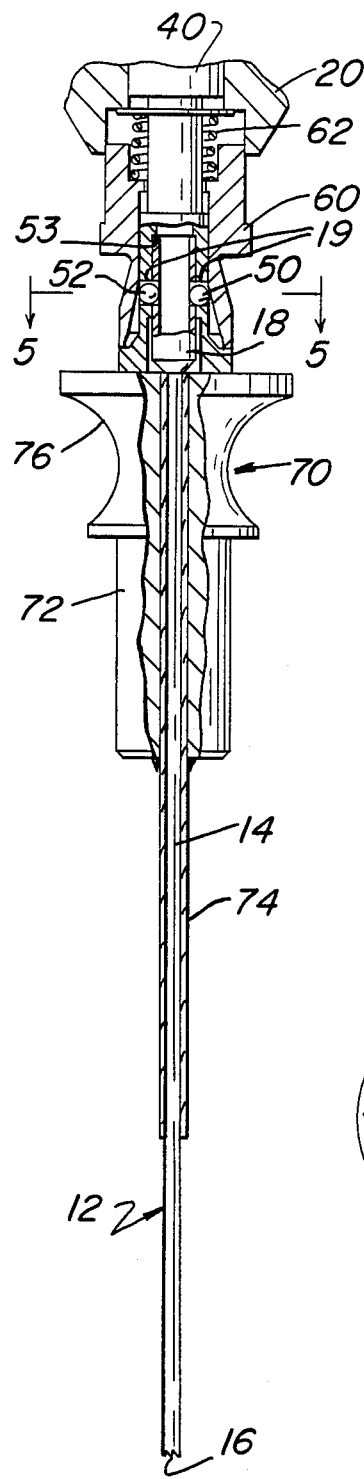
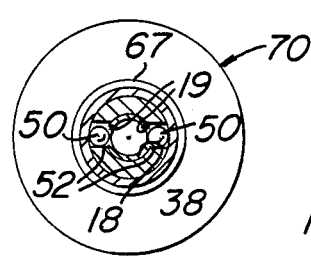
FIG. 5
FIG. 4
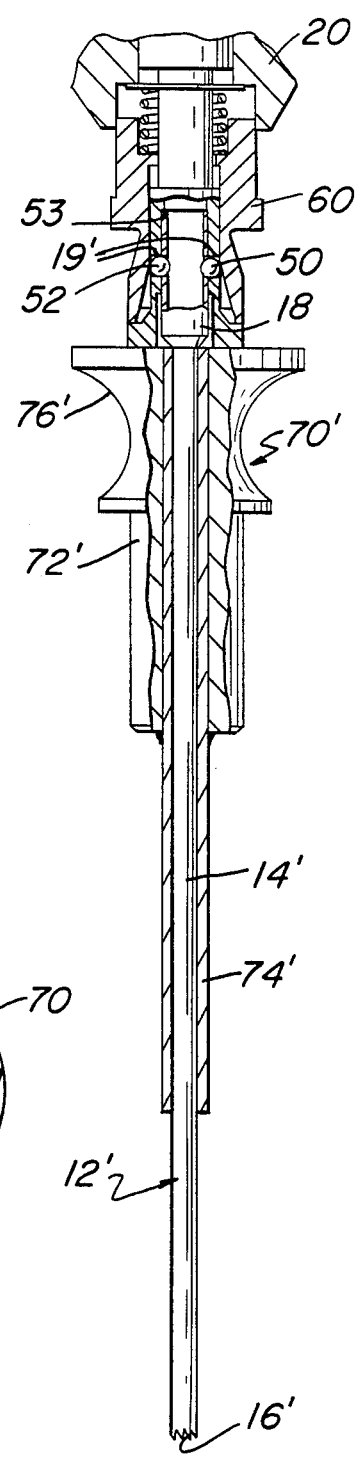
FIG. 6

BONE BORING INSTRUMENT

BACKGROUND OF THE INVENTION

1. Field of the Invention

This invention relates to instruments for the boring of bones to remove a cylindrical section of bone for medical purposes. For example, the purpose of the bone removal may be for a biopsy, the extraction of pins, screws or other foreign bodies, or as a preparatory step for other procedures such as in the harvesting of small amounts of bone-graft material.

2. Description of the Prior Art

There are a number of instruments of the indicated type currently available on the market, such as, for example, the CORB Counterrotating Biopsy Needle manufactured by Zimmer Manufacturing Company, the Bordier Trephine, the Zimmer Bone Biopsy needle manufactured by the Zimmer Manufacturing Company, and the Lane-Trent Biopsy Needle.

The present-day instruments on the market are available as either manual or power-operated devices. One of the main problems with the manual devices in use today is that they require the surgeon to "bore" his way through bone in a procedure which requires him to re-grip the instrument after each turn. This affects the quality of the "cut" and makes the procedures cumbersome for the surgeon. A major problem with the power-operated devices is that they often produce cores of bone which, on histologic inspection, are filled with bone dust and debris thereby obscurring detail. Another problem with prior art devices is that they are incapable of use throughout a range of metabolic bone diseases that include brittle as well as sclerotic (hard) bone.

SUMMARY OF THE INVENTION

The bone boring instrument of the invention is designed to obviate the problems of the present-day prior art devices. Accordingly, the instrument of the invention is provided with a one-way drive means which allows the surgeon to comfortably oscilate his hand motion while the instrument cuts bone in one direction only. Further, by allowing the surgeon to perform the boring operation without the need of letting go or re-gripping the handle, cores of bone providing good detail can be provided. Also, the instrument in accordance with the invention is provided with a trephine engaging mechanism which allows the interchangeability of trephines so that trephines with different types of saw teeth and different sizes can be used whereby the instrument is readily adaptable for use with a range of bone diseases.

Briefly stated, the above and other objects and features of the invention are provided by a bone boring instrument which comprises at least one trephine and a handle means for engaging and causing rotation of the trephine about its longitudinal axis for cutting a cyindrical core of bone for removal purposes. The handle means includes a body having a longitudinally extending central bore, and a drive shaft supported on the body for rotation within the central bore. The means for supporting the drive shaft on the body includes means for providing one-way driving engagement between the body and the drive shaft so that when the body is caused to rotate in one direction relative to the drive shaft, there is caused conjoint movement of the drive shaft and body, and when the body is caused to rotate in the opposite direction relative to the drive shaft, the body can move freely relative to the drive shaft. There is also provided a quick-release coupling means on an extended portion of the drive shaft for releasably engaging the trephine at an enlarged head portion.

BRIEF DESCRIPTION OF THE DRAWINGS

FIG. 1 is a perspective view showing the handle means of the bone boring instrument in accordance with the invention.

FIG. 2 is a longitudinal sectional view of the handle means shown in FIG. 1.

FIG. 3 is a sectional view of a detail showing the trephine engaging mechanism of the handle means in an alternate position.

FIG. 4 is a sectional view showing the handle means of FIGS. 1-3 in driving engagement with one type of trephine contained in a guide sleeve.

FIG. 5 is a sectional view taken on lines 5—5 of FIG. 4.

FIG. 6 is a view showing the handle means of FIGS. 1-3 in engagement with a second type of trephine contained in a guide sleeve.

DETAILED DESCRIPTION OF THE PREFERRED EMBODIMENT

Figure 7:
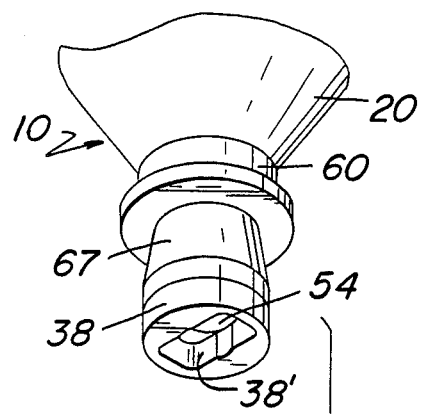
FIG. 7 is a perspective view of another embodiment of the invention.

Referring to the Drawings, the bone boring instrument of the invention comprises a handle means 10 constructed and arranged to engage and cause rotation of a trephine about its longitudinal axis for removing a cylindrical section of bone for medical purposes. A trephine is a tool well known in the medical art and comprises a circular saw having an elongated strong hollow metal shaft to which is attached means for causing rotation thereof. In use, a trephine functions to remove cylindrical sections of bone from a patient.

One trephine 12 for use with the handle means 10 is shown in FIG. 4 and comprises a hollow tubular portion 14 having circularly arranged saw teeth 16 at the distal end thereof and having an enlarged cylindrical head portion 18 at the proximal end thereof. The enlarged head portion 18 is also hollow and is provided with a pair of aligned, diametrically opposed transverse bores 19 for use in providing engagement between the trephine 12 and the handle means 10 as will be described hereafter.

Handle means 10 comprises a body 20 having a longitudinally extending central bore 22. A generally circular cap 24 is secured, by a threaded engagement shown in FIG. 2, at the upper end of body 20 and has formed on the exterior thereof recessed portions 26 forming an undulated rim. As is best shown in FIG. 1, the recessed portions 26 are designed to be readily gripped by the fingers of the surgeon in order to apply a rotating movement to the handle means 10 during the use of the bone boring instrument.

Handle means 10 also comprises a drive shaft 30 extending longitudinally within central bore 22. Means are provided for supporting drive shaft 30 on body 20 for rotation within central bore 22. Such means includes a rolling bearing means in the form of a ball bearing 32 for rotatably supporting drive shaft 30 at the upper end thereof as viewed in FIG. 2. Ball bearing 32 has its inner race positioned on the outer surface of drive shaft 30 and its outer race positioned on an enlarged bore portion 34 of the central bore 22. Ball bearing 32 is held in bore portion 34 by cap 24. Shaft 30 is provided with a pair of annular collars 31 and 33 on opposite sides of the ball bearing 32. By this arrangement, ball bearing 32 carries any axial load applied to shaft 30 during the use of the instrument.

In accordance with the invention, the instrument comprises means for providing one-way driving engagement between body 20 and drive shaft 30 so that when body 20 is caused to rotate in one direction relative to drive shaft 30 (clockwise as viewed from the top of FIG. 2), said last-named means causes conjoint movement of drive shaft 30 and body 20, and when body 20 is caused to rotate in the opposite direction relative to drive shaft 30 (counterclockwise as viewed from the top of FIG. 2), body 20 can move freely relative to drive shaft 30. The one-way drive means shown in the Drawings comprises a roller clutch means 40 mounted in the central bore 22 with its outer surface in contact with the inner wall of the bore 22 and with the drive shaft 30 extending centrally therethrough. More specifically, the roller clutch means 40 comprises a type RCB-FS clutch and bearing assembly manufactured by the Torrington Company. This clutch and bearing assembly comprises an outer housing, or cage, which is engaged by a press fit with the inner wall of central bore 22, and stainless steel springs inserted within the cage to position rollers for instantaneous lockup or driving engagement with the drive shaft 30 (whereby body 20 and drive shaft 30 move conjointly). This type of device is well known in the art and is readily available.

It will be apparent that various types of one-way drive mechanisms may be employed to provide the above-described driving engagement between the body 20 and the drive shaft 30.

The lower end of drive shaft 30 extends from the lower end of body 20 and projects downwardly from a counterbore 36 in body 20. This extended end 38 of drive shaft 30 has a hollow tubular configuration at the lower end thereof as is best shown in FIGS. 2 and 3.

In accordance with the invention, there is provided quick-release coupling means on the extended end 38 of the drive shaft 30 for releasably engaging the trephines at the enlarged head portions thereof. To this end, the quick-release coupling means comprises a pair of steel balls 50 contained in diametrically opposed transverse bores 52 in the hollow extended end 38 of the drive shaft 30. As is apparent from a consideration of FIGS. 2 and 3, balls 50 are freely movable in transverse bores 52 between a position, as shown in FIG. 2, wherein the balls 50 project into the internal bore 54 of the drive shaft 30 and a position, as shown in FIG. 3, wherein the balls 50 are clear of the internal bore 54.

The quick-release coupling means of the invention also comprises a ball retainer 60 mounted on the exterior of the extended end 38 of drive shaft 30 for sliding movement between a ball retaining position shown in FIG. 2 and a ball releasing position shown in FIG. 3. There is provided a spring means for biasing the ball retainer 60 toward said ball retaining position, such spring means comprising a compression coil spring 62 positioned in compression between an annular spring retainer 64 at the upper end of counterbore 36 in the lower end of body 20 and the end of a counterbore 66 in the upper end of the ball retainer 60.

The upper portion of ball retainer 60 is provided with a cylindrical external surface 61 adapted to be slidably received in counterbore 36 of body 20 for guiding ball retainer 60 for movement between the ball retaining and ball releasing positions shown in FIGS. 2 and 3. As ball retainer 60 is moved manually upwardly from the ball retaining position of FIG. 2 to the ball releasing position of FIG. 3, the coil spring 62 is compressed. However, spring 62 always maintains a bias on ball retainer 60 toward the ball retaining position of FIG. 2.

Ball retainer 60 has a reduced diameter portion 67 at its lower end. Portion 67 provides a diverging internal wall 68 in the area overlying and surrounding the balls 50 as is apparent from a consideration of FIGS. 2 and 3. In the ball retaining position of FIG. 2, the smaller diameter portion of wall 68 is aligned with balls 50 and comes into contact with balls 50 to maintain them in their inward position whereby balls 50 project into internal bore 54 of drive shaft 30. In the ball releasing position shown in FIG. 3, the larger diameter portion of wall 68 is aligned with balls 50 to allow the balls 50 to move radially out of internal bore 54, as is apparent from a consideration of FIG. 3.

In the use of the quick-release coupling means, ball retainer 60 is moved manually to the ball releasing position of FIG. 3 and a trephine, such as trephine 12, is inserted with its enlarged cyindrical head portion 18 extending within internal bore 54. The insertion of the enlarged head portion 18 is stopped at a small annular stop 53 formed at the upper end of internal bore 54 (see FIG. 4 which shows trephine 12 in the fully inserted position). When trephine 12 is stopped at the fully inserted position, the transverse bores 19 in the enlarged head portion 18 of trephine 12 are spaced from stop 53 the same distance as the transverse bores 52 and balls 50 in the extended end of shaft 30, whereby bores 19 and 52 can be aligned by rotating head portion 18 of trephine 12 within internal bore 54. The ball retainer 60 is then released whereupon spring 62 urges the same toward the ball retaining position shown in FIG. 2. This brings the diverging wall 68 into contact with the balls 50 to urge them radially inwardly, and when the enlarged head portion 18 of trephine 12 is turned within internal bore 54 to bring the bores 19 in alignment with bores 52, the balls 50 will be urged into engagement within bores 19 (as shown in FIG. 4) to retain the trephine 12 in the operative position engaged with the extended end 38 of drive shaft 30. The trephine 12 will then move with the drive shaft 30 during the turning thereof in one direction by the surgeon during a bone boring operation.

When it is desired to remove the trephine 12, the ball retainer 60 is pulled manually upwardly from the position shown in FIGS. 2 and 4 to the position of FIG. 3 allowing the balls 50 to move outwardly in response to a separating movement applied to the trephine 12.

The complete bone boring instrument as used by a surgeon is shown in FIG. 4. The instrument comprises the handle means 10 and a trephine 12 coupled on the extended end thereof by the quick-release coupling means as described above. The trephine 12 is positioned within a guide sleeve means 70, which comprises a body 72 having an elongated tube 74 mounted therein. The body 72 has a concave portion 76 adapted to be held by the fingers of one hand of the surgeon while the surgeon holds the handle means 10 in his other hand. During the use of the instrument, the guide sleeve means 70 has the tubular portion 14 of a trephine 12 slidably and rotatably held within tube 74 as shown in FIG. 4 and provides a guide for the trephine 12 as the surgeon performs the bone boring operation.

In FIG. 6 there is shown another trephine 12' similar to the trephine 12 whereby corresponding parts have been given the same reference numerals with primes added. Thus, the trephine 12' is adapted for use with the handle means 10 and comprises a hollow tubular portion 14' having circularly arranged saw teeth 16' at the distal end thereof and having an enlarged cylindrical head portion 18' at the proximal end thereof. Head portion 18' is hollow and has a pair of aligned, diametrically opposed transverse bores 19' for use in providing with engagement between the trephine 12' and the balls 50 of the handle means 10 as described above. Trephine 12' is essentially identical with trephine 12 except that the tubular portion 14' and the circular teeth 16' are of a larger diameter. Trephine 12' is provided with an associated guide sleeve means 70' similar to guide means 70 for use with trephine 12. The guide sleeve means 70' is provided with a body 72' having a finger receivable concave portion 76' and an elongated tube 74' adapted to slidably receive the tubular portion 14' of trephine 12' for guiding the same. The head portion 18' and the bores 19' of trephine 12' are identical to the corresponding head portion 18 and bores 19 of trephine 12 so as to be interchangeably engageable with the quick-release coupling means of the handle means 10 as described above.

The commercially available bone boring instrument in accordance with the invention is provided with many trephines and associated guide sleeve means including different types of saw teeth and different sizes whereby the instrument is readily adaptable for use with a range of bone diseases.

It will be apparent that in the use of the instrument in accordance with the invention, the surgeon can hold the handle means 10 in his right hand while holding a trephine containing guide sleeve means in his left hand with the trephine's distal end saw teeth 16 exposed for contact with the patient. In use the surgeon can comfortably oscillate his right hand and handle means 10 in a clockwise and counterclockwise motion whereby the instrument will cut bone during the clockwise rotation only. When the surgeon moves his right hand and the handle means 10 in the counterclockwise direction, the trephine will not be moved, but will remain stationary in engagement with the bone of the patient. By allowing the surgeon to perform the boring operation without the need of letting go or re-gripping the handle, the surgeon can perform precise work and it is possible to obtain high quality cores of bone.

Figure 9:
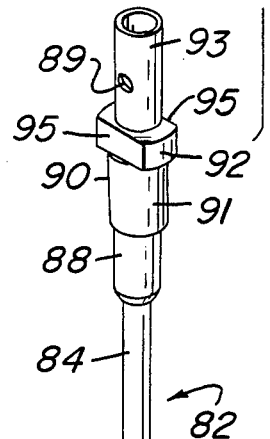
FIG. 9 is a sectional view taken on line 9—9 of FIG. 8.
Figure 9:
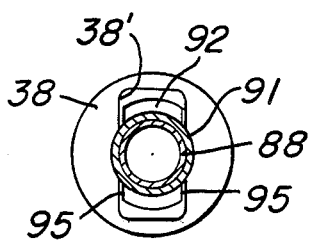
Figure 8:
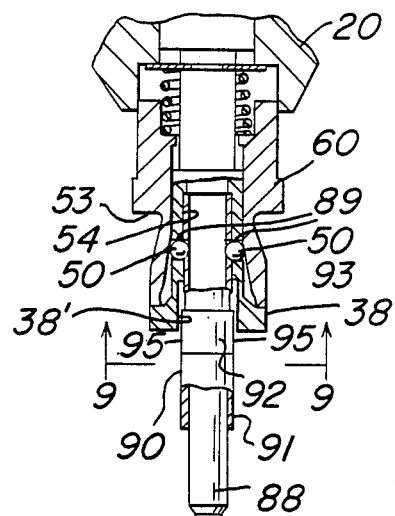
FIG. 8 is a sectional view of the FIG. 7 embodiment.
Figure 8:
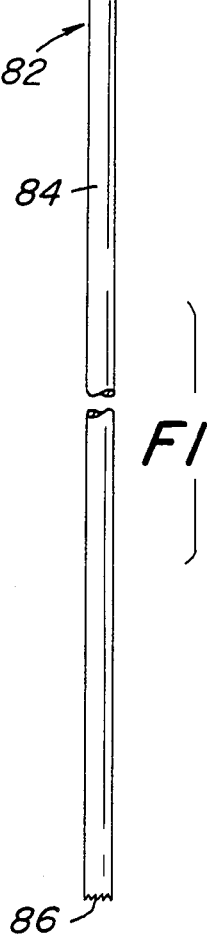

FIGS. 7-9 show an embodiment of the invention comprising a modified trephine, and a modified extended end of the handle means cooperating therewith, whereby there is provided easier alignment and better torque capability between the handle means and the trephine.

To this end, there is provided a trephine 82 similar in construction to trephine 12 and comprising a hollow tubular portion 84 similar to the tubular portion 14 of trephine 12. Thus, tubular portion 14 has circularly arranged teeth 86 at the distal end thereof and has an enlarged head portion 88 at the proximal end thereof. Head portion 88 is similar to head portion 18 of trephine 12 except that it is not provided with any transverse bores. Instead, there is provided an adapter 90 which is welded to the head of trephine 82.

Adapter 90 has a hollow tubular construction including an enlarged diameter lower portion 91 adapted to receive the head 88 of trephine 82. The adapter 90 is welded to the head 38 at the overlapping cylindrical portions of head 88 and lower portion 91 to form a unitary structure. Adapter 90 is provided with an upper hollow tubular portion 93 provided with a pair of aligned, diametrically opposed bores 89 for use in providing engagement between the trephine 82 and the handle means 10. To this end, the bores 89 are located in the same manner as the bores 19 of trephine 12 and accordingly are adapted to cooperate with the balls 50 of the quick-release coupling means on the extended end 38 of the drive shaft 30 of handle means 10 in the manner described above with respect to the emodiment shown in FIGS. 1-6.

Adapter 90 is provided with a laterally extending key portion 92 providing a pair of spaced apart parallel walls 95. The extended end 38 of the drive shaft 30 is provided with a generally rectangular bottom opening 38' adapted to receive key portion 92 with slidable contact with the parallel sidewalls 95 thereof. As is apparent from FIGS. 7-9, trephine 82 is releasably engageable with the quick release coupling means on the extended end of drive shaft 30.

In order to engage the trephine 82 on the extended end 38, the tubular portion 93 is inserted upwardly through the bottom opening 38' into the bore 54 in extended end 38 up to stop 53 with key portion 92 being oriented to slide into the rectangular opening 38' with the sidewalls 95 in engagement with the cooperating sidewall portions of opening 38' to a position as shown in FIG. 8. In this position, bores 89 are aligned with balls 50 which move into engagement therewith.

The insertion and removal of the trephine 82 is the same as that described above with respect to trephine 12, the only difference being that the cooperation between the walls 95 and opening 38' orient the trephine 82 to a desired relative position with respect to extended end 38 such that the openings 89 are aligned with the balls 50 as the trephine is moved upwardly into the position as shown in FIG. 8. This achieves an easier alignment of the trephine 82 in the handle means 10. In addition, once the trephine 82 is engaged in the position as shown in FIG. 8 within the extended end 38 of the drive shaft 30, when the handle means 10 is turned, the cooperation of the walls of the opening 38' with the sidewalls 95 provide an improved torque capability as compared with the embodiments shown in FIGS. 1-6.

It will be apparent that various changes may be made in the construction and arrangement of parts without departing from the scope of the invention as defined by the following claims.

What is claimed is:

1. A manually operable bone boring instrument for removing, by the hand manipulation of the user, a cylindrical section of bone for a medical purpose comprising:
   an elongated trephine having a hollow shaft, circularly-arranged saw teeth at the distal end thereof and an enlarged head portion at the proximal end thereof, and
   a handle means for engaging and causing rotation of said trephine about its longitudinal axis for cutting a cylindrical core of bone for removal,
   said handle means including
   a body having a longitudinally extending central bore, a drive shaft extending longitudinally within said central bore, means for supporting said drive shaft on said body for rotation within said central bore including means for providing one-way driving engagement between said body and said drive shaft so that when said body is caused to rotate in one direction relative to said drive shaft, said means for providing one-way driving engagement causes conjoint movement of said drive shaft and said body, and when said body is caused to rotate in the opposite direction relative to said drive shaft, said body is free to rotate freely relative to said drive shaft, so that the user can by an oscillating hand motion on said handle means perform a manual bone cutting operation by rotating the trephine in only one direction without letting go of said handle means, said drive shaft having an end portion extending from one end of said body, and quick-release coupling means on said extended portion of said drive shaft for releasably engaging said trephine at said enlarged head portion thereof.

2. A bone boring instrument according to claim 1 wherein said means for supporting said drive shaft on said body includes rolling bearing means for rotatably supporting said drive shaft on said body and positioned in contact with the outer surface of said drive shaft and the surface of said central bore.

3. A bone boring instrument according to claim 1 wherein said extended end portion of said drive shaft has a hollow tubular configuration, said quick-release coupling means including a pair of balls contained in a pair of diametrically opposed transverse bores in said extended end portion of said drive shaft, said balls being freely movable in said transverse bores, a ball retainer mounted on the exterior of said extended end portion of said drive shaft for movement between a ball retaining position and a ball releasing position, said ball retainer being constructed and arranged to contact said balls in said ball retaining position to maintain said balls in a position projecting into the hollow interior of said extended end portion of said drive shaft and being constructed and arranged so that in said ball releasing position said ball retainer permits said balls to move diametrically outwardly out of said hollow interior of said extended end portion of said drive shaft, and spring means for biasing said ball retainer toward said ball retaining position.

4. A bone boring instrument according to claim 2 wherein said extended end portion of said drive shaft has a hollow tubular configuration, said quick-release couping means including a pair of balls contained in a pair of diametrically opposed transverse bores in said extended end portion of said drive shaft, said balls being freely movable in said transverse bores, a ball retainer mounted on the exterior of said extended end portion of said drive shaft for movement between a ball retaining position and a ball releasing position, said ball retainer being constructed and arranged to contact said balls in said ball retaining position to maintain said balls in a position projecting into the hollow interior of said extended end portion of said drive shaft and being constructed and arranged so that in said ball releasing position said ball retainer permits said balls to move diametrically outwardly out of said hollow interior of said extended end portion of said drive shaft, and spring means for biasing said ball retainer toward said ball retaining position.

5. A bone boring instrument according to claim 1 wherein said means for providing one-way driving engagement between said body and said drive shaft comprises a roller clutch means of the type including a clutch and bearing assembly.

6. A bone boring instrument according to claim 2 wherein said mean for providing one-way driving engagement between said body and said drive shaft comprises a roller clutch means of the type including a clutch and bearing assembly.

7. A bone boring instrument according to claim 1 wherein said handle means comprises a cap secured at one end of said body and providing finger gripping portions on the exterior of said handle means.

8. A bone boring instrument according to claim 1 including at least one additional trephine having a hollow shaft of a different diameter than the diameter of said hollow shaft of said first-mentioned trephine, each of said trephines having an enlarged head portion at the proximal end thereof of the same diameter and adapted to be releasably engageable with said quick-release coupling means whereby each of said trephines is interchangeably engageable on the handle means.

9. A bone boring instrument according to claim 8 including guide sleeves associated with each of said trephines and having a central passageway adapted to slidably receive said associated trephine.

10. A bone boring instrument according to claim 1 wherein said enlarged head portion of said trephine comprises a key portion, and wherein said extended portion of said drive shaft is provided with means defining an opening at the lower end thereof adapted to receive and cooperate with said key portion to orient the trephine relative to the quick release coupling means in an engaged position thereof.

11. A bone boring instrument according to claim 10 wherein said key portion and said opening defining means comprise cooperating walls for providing driving engagement between the extended end portion of said drive shaft and the trephine.

* * * * *